(12) United States Patent
Nuhu et al.

(10) Patent No.: US 9,146,228 B2
(45) Date of Patent: Sep. 29, 2015

(54) DETERMINATION OF POLYCYCLIC AROMATIC HYDROCARBONS IN WATER USING NANOPOROUS MATERIAL PREPARED FROM WASTE AVIAN EGG SHELL

(71) Applicant: KING FAHD UNIVERSITY OF PETROLEUM AND MINERALS, Dhahran (SA)

(72) Inventors: Abdulmumin A. Nuhu, Dhahran (SA); Chanbasha Basheer, Dhahran (SA); Amjad Ashfaque Shaikh, Dhahran (SA); Abdul Rahman Al-Arfaj, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 58 days.

(21) Appl. No.: 14/049,998

(22) Filed: Oct. 9, 2013

(65) Prior Publication Data

US 2015/0099308 A1    Apr. 9, 2015

(51) Int. Cl.
*G01N 33/18* (2006.01)
*G01N 1/18* (2006.01)
*G01N 33/50* (2006.01)
*G01N 30/68* (2006.01)

(52) U.S. Cl.
CPC ............ *G01N 33/50* (2013.01); *G01N 33/1826* (2013.01); *G01N 30/68* (2013.01); *Y10T 436/212* (2015.01); *Y10T 436/255* (2015.01); *Y10T 436/25375* (2015.01)

(58) Field of Classification Search
CPC . G01N 30/68; G01N 33/1826; G01N 33/241; G01N 33/28; G01N 33/50; Y10T 436/20; Y10T 436/200833; Y10T 436/21; Y10T 436/212; Y10T 436/25; Y10T 436/25375; Y10T 436/255
USPC ........... 436/79, 127, 128, 139, 140, 161, 174, 436/177, 178; 422/68.1, 69, 72, 89, 527, 422/533
See application file for complete search history.

(56) References Cited

U.S. PATENT DOCUMENTS

| | | | |
|---|---|---|---|
| 5,496,741 | A | 3/1996 | Pawliszyn |
| 5,576,217 | A | 11/1996 | Hsu |
| 6,802,227 | B2 | 10/2004 | Lindgren et al. |
| 6,899,294 | B2 | 5/2005 | MacNeil |
| 7,678,351 | B2 | 3/2010 | Iyer et al. |
| 2010/0068821 | A1* | 3/2010 | St. Germain ................ 436/140 |

FOREIGN PATENT DOCUMENTS

KR   2006-0042798   5/2006

OTHER PUBLICATIONS

Nuhu et al. Journal of Nanomaterials, vol. 2012, Article ID 305691, pp. 1-7, 2012.*

* cited by examiner

*Primary Examiner* — Maureen Wallenhorst
(74) *Attorney, Agent, or Firm* — Oblon, McClelland, Maier & Neustadt, L.L.P.

(57) ABSTRACT

Nanoporous polymorphic crystals of $CaCO_3$ were used as sorbent and were applied in the dispersive micro-solid-phase extraction of selected polycyclic aromatic hydrocarbons as target analytes. After separation of the analytes on gas chromatography, they were successfully quantified with external calibration using flame ionization detection. Performance of the dispersive micro-solid-phase extraction was compared with a previously optimized solid-phase extraction technique.

5 Claims, 5 Drawing Sheets

DETERMINATION OF POLYCYCLIC AROMATIC HYDROCARBONS IN WATER USING NANOPOROUS MATERIAL PREPARED FROM WASTE AVIAN EGG SHELL

BACKGROUND OF THE INVENTION

1. Technical Field

The present invention relates to a biocompatible sorbent having a vateritic nanoporous structure, a method in which the sorbent is obtained, and a method in which the sorbent is incorporated into a solid phase extraction measurement method for determining polycyclic aromatic hydrocarbon content.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In recent times, the search for new advanced materials has been the focus of numerous research interests. Due to their potential applicability, researchers are now dedicating much effort to the study of these materials, with continuous inspiration derived from nature through Biomimicry—a recent research area that seeks to understand and take inspiration from natural phenomena in order to solve human problems (R. Lakshminarayanan, et al., "Structure-function relationship of avian eggshell matrix proteins: a comparative study of two major eggshell matrix proteins, ansocalcin and OC-17", *Biomacromolecules*, vol. 6, no. 2, pp. 741-751, 2005—incorporated herein by reference in its entirety). Of particular interest are the biomineralization processes by which living organisms produce minerals often to harden existing tissues. An example is the eggshell which is predominantly composed of calcium carbonate ($CaCO_3$) (S. Suzuki, "Black tea adsorption on calcium carbonate: A new application to chalk powder for brown powder materials", *Colloid Surface A*, vol. 202, no. 1, pp. 81-91, 2002—incorporated by reference herein in its entirety). In the field of analytical chemistry, great attention has been paid to nanoporous materials from different sources including $CaCO_3$ from waste avian eggshells. The electrostatic nature of $CaCO_3$ particle and its porous architecture make it a promising candidate as a solid sorbent for the extraction of polycyclic aromatic hydrocarbons (PAHs).

PAHs are ubiquitous pollutants that are found in different environmental matrices at different concentrations (G. D. Nessim et al., "Precursor gas chemistry determines the crystallinity of carbon nanotubes synthesized at low temperature", Carbon, vol. 49, no. 3, pp. 804-810, 2011; H. Yin et al., "Polycyclic aromatic hydrocarbons (PAHs) pollution recorded in annual rings of gingko (*Gingko biloba* L.): Regression analysis and comparison to other pollutants" *Microchemical Journal*, vol. 98, no. 2, pp. 303-306, 2011— each incorporated herein by reference in its entirety). Significant accumulation of PAHs in the aquatic ecosystem had been caused by anthropogenic inputs like oil spills, sea navigation, urban runoff, water and industrial wastes (B. Wu et al., "Risk assessment of polycyclic aromatic hydrocarbons in aquatic ecosystems", *Ecotoxicology*, vol. 20, no. 5, pp. 1124-1130, 2011; Y-W. Hong et al., "Accumulation and biodegradation of phenanthrene and fluoranthene by the algae enriched from a mangrove aquatic ecosystem", *Marine Pollution Bulletin*, vol. 56, no. 8, pp. 1400-1405, 2008; P. A. H. Westley et al., "Natural habitat change, commercial fishing, climate, and dispersal interact to restructure an Alaskan fish metacommunity" *Oecologia*, vol. 163, no. 2, pp. 471-484, 2010—each incorporated by reference herein in its entirety). High concentrations of PAHs are found in marine coastal environment near cities and industrial plants (K. Opuene et al., "Identification of perylene in sediments: Occurrence and diagenetic evolution", *International Journal of Environmental Science and Technology*, vol. 4, no. 4, pp. 457-462, 2007—incorporated by reference herein in its entirety). Initially, concern about PAHs was only focused on their carcinogenic property (P. Boffetta et al., "Cancer risk from occupational and environmental exposure to polycyclic aromatic hydrocarbons", *Cancer Causes and Control*, vol. 8, no. 3, pp. 444-472, 1997; H. Rubin, "Synergistic mechanisms in carcinogenesis by polycyclic aromatic hydrocarbons and by tobacco smoke: a bio-historical perspective with updates", *Carcinogenesis*, vol. 22, no. 2, pp. 1903-1930, 2001—each incorporated herein by reference in its entirety). Recently, however, searchlight has been beamed on their antagonism of hormonal functions and their potential effect on reproduction in humans, as well as their ability to depress immune function (H. Uppstad et al., "Sex differences in susceptibility to PAHs is an intrinsic property of human lung adenocarcinoma cells", *Lung Cancer*, vol. 71, no. 3, pp. 264-270, 2011—incorporated by reference herein in its entirety). These concerns have prompted both the World Health Organization (WHO) (WHO. Guidelines for Drinking Water Quality, First Addenndum to Third Edition, Geneva, 2006—incorporated by reference herein in its entirety) and the United States Environmental Protection Agency (USEPA) (U.S. EPA. National Primary Drinking Water Standards, 2003—http://www.epa.gov/safewater March 2011—incorporated herein by reference in its entirety) to formulate regulations for the protection of drinking and source water systems in order to safeguard the populace from such harmful pollutants, many of which are considered as potential carcinogens. For many superficial water systems, the European Union (EU) has set maximum admissible concentrations of 100 ng/L for both anthracene and fluoranthene, and 1200 ng/L for naphthalene (E.U. Directive 2008/105/EC, 2008, Official Journal of the European Communities L-348/84 (24 Dec. 2008), Council Directive (16 Dec. 2008) on environmental quality standards for water policy—incorporated herein by reference in its entirety).

Development of methodologies for the analysis of PAHs is, therefore, one of the important aspects of environmental analytical chemistry (N. Li et al., "Solid-phase extraction of polycyclic aromatic hydrocarbons in surface water. Negative effect of humic acid", *Journal of Chromatography A*, vol. 921, no. 2, pp. 255-263, 2001—incorporated herein by reference in its entirety). In this regard, on-line and off-line solid-phase extraction (SPE) has been widely studied for trace analysis of PAHs (Y-Y. Zhou et al., "Exploration of coordination polymer as sorbent for flow injection solid-phase extraction on-line coupled with high-performance liquid chromatography for determination of polycyclic aromatic hydrocarbons in environmental materials" Journal of Chromatography A, vol. 1116, no. 1-2, pp. 172-178, 2006—incorporated herein by reference in its entirety). It can be combined with gas chromatography-mass spectrometry (GC-MS) or gas chromatography-flame ionization detector (GC-FID). Unfortunately, due to their mainly non-polar nature and adsorption onto walls of extraction vessels, PAHs are not very amenable for multistep extraction procedures such as SPE and liquid-liquid extraction (G. A. Junk et al., "Organics in water: solid phase extraction on a small scale", *Analytical Chemistry*, vol. 60, no. 5, pp. 451-454, 1998; M. Rezaee et al., "Determination of organic compounds in water using dispersive liquid-liquid microextraction", *Journal of Chromatography A*, vol. 1116, no. 1-2, pp. 1-9; S. Lundstedt et al., "Pressurised liquid extraction of polycyclic aromatic hydrocarbons from contaminated soils", *Journal of Chromatography A*, vol. 883, no. 1-2, pp. 151-162, 2000; T. Guilherme et al., "Comparison Between Different Extraction (LLE and SPE) and Determination (HPLC and Capillary-LC) Techniques in the Analysis of Selected PAHs in Water Samples", *Journal of Liquid Chromatography and Related Technologies*, vol. 28, no. 19, pp. 3045-3056, 2005; P. K. Wong et al., "The accumulation of polycyclic aromatic hydrocarbons in lubricating oil over time—a comparison of supercritical fluid and liquid-liquid extraction methods", *Environmental Pollution*, vol. 112, no. 3, pp. 407-415, 2001—each incorporated herein by reference in its entirety). These techniques may also involve large solvent volumes which may not be in consonance with good environment-conscious practices. A greener approach should involve fewer steps and minimization of solvent waste. Solvent minimization through the use of commercial polymeric materials for sorption in solid-phase microextraction (SPME) (H. Bagheri et al., "An aniline-based fiber coating for solid phase micro extraction of polycyclic aromatic hydrocarbons from water followed by gas chromatography-mass spectrometry", *Journal of Chromatography A*, vol. 1152, no. 1-2, pp. 168-174, 2007; R. B. Gomes et al., "Determination of total and available fractions of PAHs by SPME in oily wastewaters: overcoming interference from NAPL and NOM", *Environmental Science and Pollution Research International*, vol. 16, no. 6, pp. 671-678, 2009; X. Yan et al., "Array capillary in-tube solid-phase microextraction: A rapid preparation technique for water samples", *Journal of Chromatography A*, vol. 1244, no. 29, pp. 69-76, 2012—each incorporated herein by reference in its entirety) and stir bar sorptive extraction (SBSE) (B. Kolahgar et al., "Application of stir bar sorptive extraction to the determination of polycyclic aromatic hydrocarbons in aqueous samples", *Journal of Chromatography A*, vol. 963, no. 1-2, pp. 225-230, 2002; J-F. Liu et al., "Use of ionic liquids for liquid-phase microextraction of polycyclic aromatic hydrocarbons", *Analytical Chemistry*, vol. 75, no. 21, pp. 5870-5876, 2003—each incorporated herein by reference in its entirety) have been attempted for the analysis of PAHs in water. However, these materials are often expensive. Alternative sorption material that can carry out this function at a lower cost and offers more convenience in handling is preferred.

Solid-phase microextraction (SPME) techniques is a favored method for sampling of analytes. References describing SPME techniques, specifically as regards to explosives detection include "Trace Analysis of Explosives in Seawater Using Solid-Phase Microextraction and Gas Chromatography/Ion Trap Mass Spectrometry", S. A. Barshick and W. H. Griest, Anal. Chem. 1998, 70, 3015-3020; "Trace Explosives Signatures from World War II Unexploded Undersea Ordnance", M. R. Darrach, A. Chujian, and G. A. Plett, Environ. Sci, Technol. 1998, 32, 1354-1358; "Application of Solid-Phase Microextraction to the Recovery of Organic Explosives", K. P. Kirkbride, G. Klass and P. E. Pigou, J. Forensic Sci., 1998, 43(1), 76-81. Each of the references cited above describes generally the use of SPME fibers. Typically, such fibers are fine (about 0.25 mm OD) silica fibers coated with a thin layer of a sorbing material. SPME fibers are often coated with a sorbent chosen or engineered to have a high propensity to sorb certain analytes of interest. The fibers are exposed to a gaseous or liquid environment from which a target analyte sample is to be extracted.

After a sample is collected, the fiber can then be conveniently inserted into a gas chromatograph (GC) by placing the fiber into the inlet of a GC apparatus. One common way to accomplish this is to use a needle to puncture a septum covering the GC inlet, and a syringe plunger to push the fiber (containing sorbed analytes) through the needle into the GC apparatus. Next, the fiber is rapidly heated to drive off the analytes sorbed to the sorbent substance coating the fiber. The analytes are then swept into the GC column for normal separation and quantitation.

Typically, SPME sampling involves placing the SPME fiber in the headspace above a contaminated or potentially contaminated test subject material (e.g., soil). Analytes then passively diffuse through the headspace and some ultimately adhere to the fiber. For gaseous samples of low concentration (such as in the case with explosives in soil gases), diffusion of the analytes through the gas to the SPME fiber can be a rate limiting step, resulting in long sampling times. This is especially true for instances wherein it is necessary for equilibrium to be reached, as is the case, frequently, in quantitation studies. "Solid-Phase Microextraction", Z. Zhang, M. J. Yang and J. Pawliszyn, Anal. Chem. 1994, 66(17), 844A-853A; "Headspace Solid-Phase Microextraction", Z. Zhang and J. Pawliszyn, Anal. Chem. 1993, 65, 1843-1853.

SPME has been shown to successfully collect target analytes in low concentration in gases and liquids. An opportunity, however, exists for optimization of SPME techniques, and further, a need remains for an optimized method and apparatus for extracting target analyte substances from volumes of gases containing those substances in low concentration. The need is especially apparent as regards to overcoming problems associated with slow equilibration and long sample times.

In another SPME process, a coated or uncoated fiber housed within a needle of a syringe is brought into contact with components/analytes in a fluid carrier or headspace above the carrier for a sufficient period of time for extraction of the analytes to occur onto the fiber or coated fiber. Subsequently the fiber is removed from the carrier or headspace above the carrier and the analytes desorbed from the fiber generally by thermal desorption into an analytical instrument, such as a gas chromatograph (GC), for detection and quantification of the analytes.

SPME has been shown to be a very useful sample preparation technique for a variety of analytes. However, SPME extraction and detection has some very serious limitations. One particularly serious limitation is in relation to attempting to utilize SPME for extractions of trace organic analytes in organic solvent carrier matrices. Basically, SPME generally cannot be applied to extraction of trace amounts of organic analytes from organic solvent carrier matrices, such as hexane. Attempts to apply SPME to extraction of trace amounts of organic analytes from organic solvents carrier matrices do not provide acceptable results because the solvent matrix is extracted by the coated fiber of the SPME device. SPME fibers for extraction of organic analytes are generally coated with an organic phase, such as the non-polar poly(dimethylsiloxane) (PDMS). Instead of the trace organic analytes being adsorbed on or into the organic phase coating on the fiber, the solvent carrier matrix components are themselves adsorbed or extracted onto the organic phase due to their overwhelmingly predominant presence in the sample. This prevents selective, efficient extraction of the trace organic analytes. For this reason SPME has not found any practical applicability for extraction of trace organic analytes from organic solvent carrier matrices. Rather, SPME carrier matrices have generally comprised predominantly aqueous matrices, for example water, a water-methanol (95:5) matrix or an aqueous inorganic salt solution matrix This is a particularly serious limitation on the use of SPME extraction procedure since many common sample enrichment and preparation techniques for organic analysis and detection of trace amounts of organic analytes in a sample involve contacting the sample with an organic solvent carrier matrix to dissolve the organic analytes in the organic solvent carrier matrix, or in some way extracting the trace organic analytes into an organic solvent carrier matrix. For example, United States Environmental Protection Agency (EPA) Methods 608 and 525.1 require liquid-liquid extraction or liquid-solid extraction of semivolatile organic compounds, such as pesticides and polyaromatic organic compounds, from aqueous samples, such as municipal and industrial discharges or drinking water, into organic solvents. Organic solvents are used because the organic solvents have a high dissolution capability/power for the organic analytes. Subsequent concentration of the extracts and analysis thereof can give reasonably good detection. However, detection sensitivity is not particularly good and generally detection of trace amounts of less than 1 ppb are difficult or impossible to obtain with a mass spectrometer. Moreover, attempts to apply SPME methodology to this type of analysis for trace organic analytes in an organic solvent carrier matrix have failed to give selective extraction of the trace organic analytes out of the organic solvent carrier matrix due to the overwhelmingly predominant presence of said organic solvent carrier matrix as mentioned hereinbefore.

Other sorbents can be used in SPME methods other than fibrous material. For example, an eggshell can be used to extract a sorbent for SPME methods. In view of the significant disposal costs for what is conventionally a waste product, and additionally, in view of current environmental practicalities which are decreasing the availability of local disposal sites (thereby further increasing disposal cost), it will be readily appreciated that finding a significant use for egg shell waste would have important financial and environmental benefits.

It is well known that the eggshell of the chicken is a biologic composite of organic matrix (membrane) and inorganic mineral (shell). The mineral of the shell is mainly calcitic calcium carbonate. The shell membranes remain non-mineralized throughout the assembly of the eggshell and the development of the embryo (Wyburn et al., 1970, Exp. Physiology 55:213). Between the shell and the membrane is a layer of foci of mineralized matrix called the calcium reserve assembly (CRA). The CRA provides the mobilized calcium for the mineralization of the skeleton of the developing embryo (Diekert et al., 1989, Poultry Science 68:1569). At the apex of each CRA is a region known as the crown The crown is a morphologically distinct structure where function is not clear. It may act to separate the resorbable calcium (CRA) and non-resorbable calcium (shell). External to the crown is the shell proper, which is approximately 250 mm in thickness and contains approximately 5 gm of calcium carbonate (Diekert et al., 1989, Poultry Science 68:1569) It is this part of the shell which acts to physically encase and protect the developing embryo (Arias et al., 1991, Matrix 11:313).

Knowledge of the various eggshell structures was critical in developing procedures for recovering and separating eggshell calcium material from the membrane. Two shell membranes surround the egg of most avian species. A thick outer membrane attached to the shell and a thin inner-membrane. Each of these membranes is composed of a network of fibers. Early studies suggested that collagen was present as indicated by hydroxylysine and the digestion of eggshell membrane by collagenase. The presence of Type I and Type V collagen were established in the membrane by Wong (Wong et al., 1984, Developmental Biology 104:28) and Arias (Arias et al., 1991, Matrix 11:313) Other studies (Leach et al., 1982 Poultry Science 61:2040) showed that a unique protein containing lysine-derived cross links was present. Recent studies have identified, among other constituents, type V and X collagen and proteoglycans (mammillan, a keratan sulfate proteoglycan, and ovoglycan, a dermatan sulfate proteoglycan), whose localization depends on a topographically defined and temporally regulated deposition. (Soledad F. et al., 2001, Matrix Biol. 19:793).

Chicken eggshells (ES), currently an environmental nuisance, are excellent reactive agglomerates that depict sustained high reactivity towards carbonation over multiple CCR cycles. The typical dry eggshell, an excellent bioceramic composite, comprises two predominantly calcitic ($CaCO_3$) layers and the innermost shell membrane layer. The organic material in the eggshell has excellent calcium binding properties and leads to a strong calcitic shell by self-organizing the calcite crystals during the natural eggshell formation process. Poultry eggs, used for a variety of products, result in massive amounts of eggshell waste that incur expensive disposal costs. The average annual per capita egg consumption in the United States is about 257 in 2001. However, annual eggshell wastes from various hatcheries and egg breaking industries amount to over 190,000 tons. Current disposal options include the most basic landfill, land applications including soil mixing and organic farming, and recycling in poultry diets. Of these, landfill is the easiest option as other alternatives involve significant processing costs. Eggshells, considered as organic wastes, require about $20-40/ton for landfill disposal in the U.S. This problem is further exacerbated in European countries where land prices are at a premium. In addition, landfill taxes in the United Kingdom increase this disposal cost to about 30-50£/ton. Therefore, the usage of refuse eggshells in this high temperature $CO_2$ capture technology as reactive agglomerates is simultaneously a comprehensive solution to two global environmental concerns.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In the present invention, a biocompatible calcium carbonate is crystallized from eggshell waste.

In another embodiment, the calcium carbonate polymorph displays a vateritic nanoporous structure.

In another embodiment, the calcium carbonate polymorph is used as a sorbent in a dispersive micro solid phase extraction (D-µ-SPE) measurement method.

In another embodiment, the calcium carbonate polymorph is used to absorb and determine polycyclic aromatic hydrocarbon (PAH) content in aqueous or organic solutions.

In another embodiment, the sorbent has a pore size of about 25 nm.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
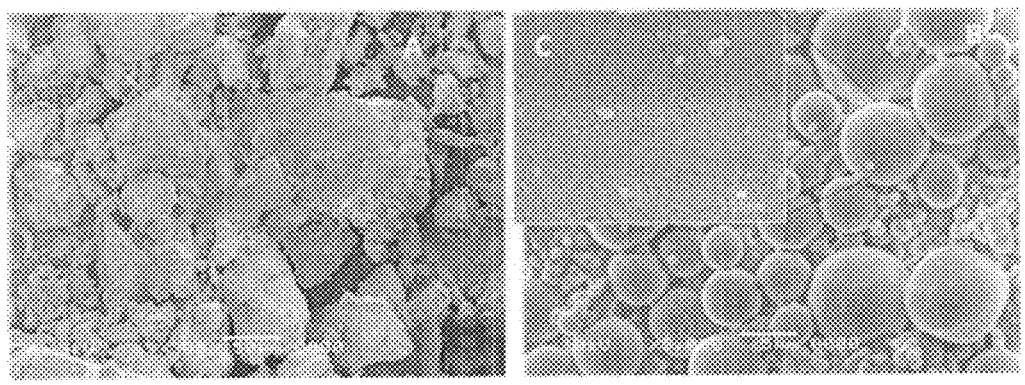
FIG. 1 is a scanning electron micrograph of grinded powder of goose eggshell and its components before and after crystallization.

Referring now to the drawings, wherein like reference numerals designate identical or corresponding parts throughout the several views.

The present invention relates to a method for obtaining a calcium carbonate material from egg shells. The method may include chemical or thermal methods of treatment to an egg shell to separate an organic component from the calcium carbonate of the eggshell. In one aspect, such chemical methods may include oxidation in which the egg shell is chemically treated with an oxidizing agent such as any hypochlorite bleach solution including sodium hypochlorite, calcium hypochlorite, lithium hypochlorite, or ammoniacal hypochlorite bleach solution, or hypobromite bleach solution including sodium hypobromite, calcium hypobromite, lithium hypobromite, or any other organic or inorganic oxidizing agents such as organic or inorganic peroxides, including hydrogen peroxide, sodium percarbonate, and sodium perborat or be exposed to an oxidizing atmosphere in which the egg shell reacts with an oxidizing atmosphere so that at least a majority preferably 60%, 75% or 95% of the desired calcium carbonate material can be separated from the organic component of the egg shell. In another aspect, thermal treatment of the eggshell may include calcination in which the eggshell undergoes thermal treatment to bring about thermal decomposition of portions of the eggshell and separation of organic components from the carbonate-containing component of the eggshell occurs.

In another aspect of the invention, mechanical treatment and physical separation may be used to separate a protein layer (e.g., an organic component) from the calcium carbonate portion of the egg shell. Such methods include but are not limited to a non-chemical separator in which water-based agitation separates the eggshell and protein membrane; mechanical abrasion in which a gas flow separates eggshell from protein membrane by cyclonic action; dissolved air-flotation separation in which eggshells are set in water, ground and separated from protein membrane and in which air is injected into water flow to obtain carbonate-containing compound that sinks in water; and a fluid tank with water and acetic acid in which eggshells are placed in a fluid tank containing water and acetic acid and cavitated to separate said eggshell membrane from eggshell.

Any carbonate-containing egg shell may be used including any avian egg shell such as chicken egg shells, duck egg shells, turkey egg shells, or quail egg shells. Preferably, quail egg shells are used. Eggshell is typically composed of 95-97% calcium carbonate while the remaining portion includes calcium phosphate and magnesium carbonate as well as soluble and insoluble proteins. The extracted calcium carbonate may contain small amounts of calcium phosphate and magnesium carbonate, e.g., less than 10% by weight, preferably less than 5%, less than 1% and less than 0.1% by weight, independently or combined. Calcium carbonate extracted from eggshells may contain impurities from proteins contained within the eggshell and said impurities may influence the growth of crystals from the calcium carbonate. Preferably, the calcium carbonate material derived from the eggshell contains no other carbonate-containing compounds including but not limited to sodium sesquicarbonate ($Na_3H(CO_3)2$), carbonic acid ($H_2CO_3$), lithium carbonate ($Li_2CO_3$), beryllium carbonate ($BeCO_3$), sodium carbonate ($Na_2CO_3$), magnesium carbonate ($MgCO_3$), potassium carbonate ($K2CO3$), rubidium carbonate ($Rb_2CO_3$), strontium carbonate ($SrCO_3$), caseium carbonate ($Cs_2CO_3$), barium carbonate ($BaCO_3$), manganese (II) carbonate ($MnCO_3$), iron (III) carbonate ($FeCO_3$), cobalt(II) carbonate ($CoCO_3$), nickel (II) carbonate ($NiCO_3$), copper (II) carbonate ($CuCO_3$), zinc carbonate ($ZnCO_3$), silver carbonate ($Ag_2CO_3$), cadmium carbonate ($CdCO_3$), thallium (I) carbonate ($Tl_2CO_3$), and lead carbonate ($PbCO_3$).

In another embodiment of the invention, said eggshells are dried and ground into small pieces. The small pieces of eggshell are treated with an oxidizing solution to separate the organic material from the inorganic material of the eggshell. The oxidizing solution may contain any hypochlorite bleach solution including sodium hypochlorite, calcium hypochlorite, lithium hypochlorite, or ammoniacal hypochlorite bleach solution, or hypobromite bleach solution including sodium hypobromite, calcium hypobromite, lithium hypobromite, or any other oxidizing agents such as peroxides, including hydrogen peroxide, sodium percarbonate, and sodium perborate. Once said eggshells are bleached, they are powdered and decalcified with either an organic or inorganic acid such as HCl, HBr, HI, $H_2SO_4$, para-toluene sulfonic acid and the like, more preferably the acid being HCl to form an aqueous solution. The pH of the solution containing the calcium carbonate dissolved in acid has a pH in the range of 3-10, more preferably in the range of 6-8. Further, the calcium carbonate-containing solution contains a mass concentration in the range of 0.01-0.5 g/mL. Preferably, the mass concentration of calcium carbonate in the solution is 0.1 g/mL.

Calcium carbonate crystals containing a monomeric vateritic structure can be grown from a solution of calcium carbonate and said acid by method of recrystallization and purification using Weiner's vapor diffusion method. Other methods of chemical recrystallization of calcium carbonate include but are not limited to single-solvent recrystallization, multi-solvent recrystallization, hot-filtration recrystallization, seeding, high throughput methods or evaporation of a single solvent to obtain said crystals from the egg carbonate. Vapor diffusion is preferred. Upon crystallization of eggshell, cations that can influence crystal growth include any Group 1 or 2 transition metals and anions that can influence crystal growth include any Group 7 halogens or any other anionically charged particle either in atomic form or in the form of a compound may influence calcium carbonate crystal growth.

Mechanical methods of crystallization may be used to produce the calcium carbonate vateritic polymorph. Mechanical methods include but are not limited to ultrasonication, in which a solution of calcium carbonate and said acid may be ultrasonicated at a frequency of >20 kHz, more preferably between 20-30 kHz. The ultrasonicator functions at a power within the range of 100-1500 W, 200-1300 W, or 300-800 W. More preferably, the ultrasonicator functions at a power between 300-800 W. Ultrasonication of the acidic solution mixed with the calcium carbonate material yields a crystal structure.

The vateritic structure that is formed from recrystallization is a polymorphic mineral of calcium carbonate ($CaCO_3$) consisting of a hexagonal crystal system. Preferably, at least 95% of the carbonate-containing material after crystallization consists of calcium carbonate. More preferably, the crystallized structure is 100% calcium carbonate.

The vateritic polymorph has a nanoporous structure with an average pore size range of 1-100 nm, preferably 5-80 nm, 10-60 nm, 15-50 nm, and 20-40 nm. More preferably, the polymorph is a material having an average pore size of about 25 nm. Further, the calcium carbonate nanoporous particles have an average particle size $D_{50}$ in the range of 0.1 µm-100 µm, 0.5 µm-80 µm, or 1.0 µm-50 µm. Preferably, the calcium carbonate nanoporous surface has a particle size distribution between 1.0 µm-50 µm, in which pore size is defined as the ratio of pore volume to the total volume. Further, porosity is a measure of the void spaces in the calcium carbonate polymorph, and is a fraction of the volume of voids over the total volume.

In another embodiment the calcium carbonate particles have a diameter in the range of 0.025-10 µm, 0.04-6 µm, or 0.05-5 µm. More preferably, the diameter is in the range of 0.05-5 µm. The sphericity, in which sphericity is defined as the ratio of the surface area of a sphere (with the same volume as the given particle) to the surface area of the polymorph has a range of 0.500-0.999, 0.600-0.950, 0.650-0.900. Preferably, the sphericity of the polymorph has a range of 0.650-0.900.

The vateritic polymorph preferably consists of vaterite but can also contain other polymorphs of calcium carbonate such as aragonite and calcite. Aragonite is a polymorphic crystalline structure derived from $CaCO_3$ having an orthorhombic system. Aragonite forms acicular crystals and repeated twinning results in pseudo-hexagonal forms. Calcite is a polymorphic crystalline structure derived from $CaCO_3$ having a trigonal-rhombohedral system. Tabular forms, prisms, or various scalenhoedra are characteristic of calcite.

The preferred polymorph has at least 50% vaterite and may contain other polymorphs such as sodium carbonate decahydrate, sodium carbonate heptahydrate, sodium carbonate monohydrate, dolomite, and magnesite. The preferred polymorphic composition includes but is not limited to the following compositional ranges: 50-100% vaterite, 0-25% calcite, and 25-50% aragonite or 50-100% vaterite, 25-50% calcite, and 0-25% aragonite or 50-100% vaterite, 10-50% calcite, and 40-50% aragonite or 70-95% vaterite, 15-30% calcite, and 15-30% aragonite or 80-95% vaterite, 5-20% calcite, and 5-20% aragonite or 80-100% vaterite, 0-20% calcite, and 0-20% aragonite. Preferably, 100% of the polymorphic calcium carbonate structure is vateritic.

EXAMPLE

Calcium Carbonate Preparation

To prepare the nanoporous $CaCO_3$ sorption material, waste avian egg shells from quails were dried and broken into small pieces. These pieces were then grinded and the coarse lump was treated with ammoniacal hypochlorite bleach solution (5%) for about 15 min to remove the egg shell membrane. 10 g of clear, bleached egg shells were powdered and decalcified with 100 mL hydrochloric acid (2M) for 12 hrs. Vateritic calcium carbonate crystals were then grown from this solution using Weiner's vapor diffusion method (R. Lakshminarayanan et al., "Formation of transient amorphous calcium carbonate precursor in quail eggshell mineralization: an in vitro study", *Biomacromolecules*, vol. 7, no. 11, pp. 3202-3209, 2006; J. Yu, et al., "Facile precipitation of monodispersed calcium carbonate spherical particles via a simple precipitation reaction", *Materials Chemistry and Physics*, vol. 88, no. 1, pp. 1-4, 2004—each incorporated herein by reference in its entirety). Vateritic balls of $CaCO_3$ were observed during precipitation reaction in the presence of organic additives (C. Wang, C. He et al., "Combination of adsorption by porous $CaCO_3$ microparticles and encapsulation by polyelectrolyte multilayer films for sustained drug delivery", *International Journal of Pharmaceutics*, vol. 308, no. 1-2, pp. 160-167, 2006—incorporated herein by reference in its entirety). These balls were of high porosity and proved to be efficient in drug delivery (J. L. Arias, et al., Eggshell Growth and Matrix Macromolecules, in "Handbook of Biomineralization: Biological Aspects and Structure Formation" E. Bäuerlein, Ed., Wiley-VCH Verlag GmbH, Weinheim, Germany, 2008—incorporated herein by reference in its entirety). The presence of inorganic and organic substances, such as magnesium ions and aspartic acid, may influence the growth of calcium carbonate and control its morphology (E. Loste et al., "The role of magnesium in stabilising amorphous calcium carbonate and controlling calcite morphologies", *Journal of Crystal Growth*, vol. 254, no. 1-2, pp. 206-218, 2003; H. Tong, et al., "Control over the crystal phase, shape, size and aggregation of calcium carbonate via a 1-aspartic acid inducing process", *Biomaterials*, vol. 25, no. 17, pp. 3923-3929, 2004—each incorporated herein by reference in its entirety). Hence, these substances can be used to adjust the porosity of the produced nanoporous material. FIG. 1A shows the eggshell scanning electron micrographs before crystallization. FIG. 1B shows the eggshell scanning electron micrographs after crystallization. FIG. 1C shows the nanoporous surface of a single calcium carbonate vateritic ball, in which about 25 nm pores can be seen.

In another embodiment of the invention, the calcium carbonate vateritic polymorph is used as a sorbent in a dispersive micro-solid-phase extraction method to determine polycyclic aromatic hydrocarbon (PAH) content in water. In the method, a sample of the calcium carbonate vateritic polymorph ranging from, for example, 25 mg-100 mg, 30-70 mg, 40-60 mg and 45-55 mg is conditioned with a solvent by ultrasonication. Preferably, 50 mg of said polymorph is used. The following solvents can be used but the method is not limited to only the following: dichloromethane (DCM), 1-octanol, n-hexane, cyclohexane, pentane, cyclopentane, 1,4-dioxane, chloroform, methanol, ethanol, propanol, toluene, xylene, benzene, diethyl ether, tetrahydrofuran, acetic acid, and acetone. Preferably a solvent containing an aromatic group is used. More preferably, the aromatic solvent contains at least one six-membered hydrocarbon ring with a $C_1$-$C_6$ alkyl group selected from the group consisting of methyl (—$CH_3$), ethyl (—$C_2H_5$), propyl (—$C_3H_7$), butyl (—$C_4H_9$), pentyl (—$C_5H_{11}$), or hexyl (—$C_6H_{13}$) where said alkyl unit is attached to one of the carbon units of said hydrocarbon ring. Preferably, the alkyl group is methyl and more preferably the aromatic solvent used is toluene.

Ultrasonication in the presence of a solvent enhances the absorbivity of the calcium carbonate nanoparticles by improving their dispersion within said solvent and optimizes conditions for adsorption of the polycyclic aromatic hydrocarbons onto the calcium carbonate sorbent once they are added to the calcium carbonate-containing solution. Ultrasonication is performed over a period of time ranging from 2-20 minutes, 2-15 minutes, and 3-10 minutes. Preferably, the calcium carbonate polymorph is conditioned for 5 minutes in an ultrasonicator. The ultrasonicator preferably functions at a frequency of >20 kHz, more preferably between 20-30 kHz. The ultrasonicator functions at a power within the range of 100-1500 W, 200-1300 W, or 300-800 W. More preferably, the ultrasonicator functions at a power between 300-800 W.

The conditioned mixture of $CaCO_3$ and solvent is mixed with an aqueous or organic sample containing one or more polycyclic aromatic hydrocarbons. An aromatic, non-polar solvent such as toluene allows for a greater enhancement factor and enhanced adsorption of the PAH's onto the nanoporous calcium carbonate polymorph. PAHs are hydrophobic and non-polar and the structure of toluene, an aromatic ring containing a methyl group, along with the hydrophilic nature of toluene is believed to allow better interaction of the PAHs within the hydrophobic areas of the calcium carbonate polymorph hexagonal crystal system.

When the calcium carbonate polymorph is used as the sorbent in D-μ-SPE method, conditioning of the calcium carbonate polymorph sorbent with the organic solvent increases the wettability of the sorbent which allows for greater adsorption of the PAHs onto the calcium carbonate polymorph. Conditioning the sorbent with the organic solvent further decreases the contact angle of the PAH adsorption onto the sorbent and increases wettability with respect to an untreated calcium carbonate sorbent, where the contact angle is higher than that of the treated sorbent. The contact angle of the PAH with the sorbent is in the range of $0°\leq\theta<180°$. More preferably, the contact angle is in the range of $0\leq\theta<90°$ and even more preferably the contact angle is 0 ($\theta=0$), where $\theta$=contact angle.

The calcium carbonate vateritic polymorph can be used to extract and/or to adsorb the following polycyclic aromatic hydrocarbons including, but not limited to acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, biphenyl, chrysene, coronene, dibenz(a,h)anthracene, fluoranthene, fluorene, indeno(1,2,3-cd)pyrene, phenanthrene, pyrene, and naphthalene. Preferably, the calcium carbonate sorbent is used to absorb and measure naphthalene, biphenyl, acenaphthene, fluorene, phenanthrene, pyrene, and fluoranthene.

The PAH-containing sample is contacted with the calcium carbonate sorbent such that the temperature of the sample and the temperature of the sorbent are substantially the same. Preferably the temperature of the sample and the sorbent do not differ from one another by more than 1° C., preferably 2, 5, 10 or 20° C.

The mixture of sample and calcium carbonate is ultrasonicated over a period of time ranging from 10-70 minutes, 20-60 minutes, 25-50 minutes, and 30-40 minutes. Preferably, the solution is ultrasonicated for 30 minutes to allow optimal adsorption. After an induction period, e.g., from 1 minute to 3 hours, preferably from 5 minutes to 2 hours, from 15 minute to 1.5 hours, and from 30 minute to 1 hour. The ultrasonicated mixture containing said sorbent and PAH analytes is centrifuged at a range of 10,000-20,000 rpm, 11,000-19,000 rpm, 12,000-18,000 rpm, and 13,000-17,000 rpm over a time period of 1-10 minutes, 1.5-8 minutes, and 2-6 minutes at a temperature ranging from 10° C.-60° C., 15° C.-50° C., and 20° C.-40° C. Preferably, the solution is centrifuged at 13,500 rpm over a time period of 2 minutes at a temperature in the range of 20° C.-40° C.

Other methods may be used to separate the analyte from said aqueous or organic solution including filtering, using adsorption chillers, or settling solution without agitation so that at least 95% of the desired adsorbed compound is obtained.

Following centrifugation, the $CaCO_3$ is treated to remove excess water. Treatment may include absorbing excess water with an absorbent such as cellulose (paper towel), decanting and/or pressing. Desorption of PAH from the treated $CaCO_3$ is subsequently performed. Desorption methods include but are not limited to ultrasonication. In said method, an excess of solvent (preferably an organic solvent) is added to the nanoporous calcium carbonate crystals. The following solvents can be used but are not limited to dichloromethane (DCM), 1-Octanol, n-Hexane, cyclohexane, pentane, cyclopentane, 1,4-dioxane, chloroform, methanol, ethanol, propanol, toluene, xylene, benzene, diethyl ether, tetrahydrofuran, acetic acid, and acetone. Preferably a solvent containing an aromatic compound is used. More preferably, the aromatic solvent is a six-membered hydrocarbon ring containing a $C_1$-$C_6$ alkyl group selected from the group consisting of methyl, ethyl, propyl, butyl, pentyl, or hexyl where said alkyl unit is attached to one of the carbon units of said hydrocarbon ring. Preferably, the alkyl group is methyl and more preferably the aromatic solvent used is toluene.

Said solvents preferably have a viscosity ranging from 0.200 cP-0.900 cP, 0.300 cP-0.800 cP consisting of a temperature ranging from 10° C.-60° C., 15° C.-50° C., and 20° C.-40° C. More preferably, the solvent has a viscosity of 0.590 cP at a temperature of 20° C. The volume of solvent added is in the range of 10 μL-200 μL, 20 μL-150 μL, 30 μL-125 μL, and 40 μL-110 μL. Preferably, the volume of said solvent added is 100 μL.

Ultrasonication is performed over a period of time ranging from 2-30 minutes, 5-25 minutes, and 10-15 minutes. Preferably, the solution is conditioned for 15 minutes in an ultrasonicator to allow for maximal desorption of the analytes. The ultrasonicator functions at a frequency of >20 kHz. The ultrasonication of said crystals allows for the analytes to be removed from the crystals for analysis in a gas-chromatography flame ionization detector machine.

In said method for extracting PAH's the enhancement factor (EF) of the extraction procedure (the ratio of GC peak areas for extracted sample relative to un-extracted one) is greater than 10 fold, preferably in the range of 50-2000 fold, 100-1800 fold, 150-1600 fold. Preferably the enhancement factor is in the range of 388-1433-fold for the corresponding analytes.

EXAMPLE

Microextraction

Individual PAH standards (99.5% purity) were purchased from Sigma (St. Louis, Mo., USA). HPLC-grade solvents were from J. T. Baker, (NJ, USA). Ultrapure water was purified in a Milli-Q-water purification system (Millipore, Bedford, Mass., USA). Standard working solution was prepared in methanol everyday using stock solution. All reagents and solvents used were of analytical or HPLC-grade unless otherwise mentioned. Seawater samples were collected from Dammam (Eastern province of Saudi Arabia) in Teflon jars in accordance with USEPA surface water sampling SOP (EPA, 1991) and analyzed on the same day. Methanol (10%, v/v) was added to these samples and mixed thoroughly in order to avoid adsorption of PAHs onto glassware. The D-μ-SPE was carried out as follows: the nanoporous vateritic $CaCO_3$ (50-mg) was first conditioned with dichloromethane (DCM) (for 5 min in ultrasonicator) and then placed in 5 mL water sample spiked with 10 μL of the mixed PAHs solution (10 μg/mL of each compound) in a 10-mL glass centrifuge vial. This was then ultrasonicated for 30 min and the resultant cloudy sample centrifuged at 13500 rpm for 2 min. The aqueous layer was discarded and the material was dabbed dry by placing it on a lint-free tissue to remove excess moisture. A 100 μL of DCM was then added to the nanoporous calcium carbonate crystals and ultrasonicated for 5 min for analyte desorption. Finally, 2 μL of DCM containing the desorbed analytes was injected into the GC-FID machine using auto sampler. In order to avoid any carryover effects, each extraction was performed using a freshly prepared nanoporous vateritic $CaCO_3$ material.

SPE experiment was performed based on previously optimized extraction conditions (F. Busettia et al., "Determination of sixteen polycyclic aromatic hydrocarbons in aqueous and solid samples from an Italian wastewater treatment plant", *Journal of Chromatography A*, vol. 1102, no. 1-2, pp. 104-115, 2006—incorporated herein by reference in its entirety).

The extraction mechanism for D-μ-SPE is similar to SPME and SBSE. Preliminary studies were conducted to investigate the most appropriate solvents (DCM, toluene, methanol and hexane) for conditioning nanoporous vateritic balls of $CaCO_3$. Conditioning with organic solvent resulted in significant improvement in the extraction performance of the nanoporous $CaCO_3$, probably due to improved wettability of the sorbent in the presence of the solvent. Other parameters that might influence the extraction efficacy of the procedure were investigated prior to using it for the determination of PAHs in real water samples. The objective of the procedure was to obtain maximum analyte recovery and sensitive determination. The parameters investigated were extraction time, sample pH, extraction solvent and desorption time. All experiments were performed in replicates of three.

Determination of PAHs was carried out using Agilent GC 7890 μL. Chromatographic separation of the seven PAHs was accomplished with a DB-1 fused-silica capillary column (30 m×0.32 mm I.D, 1 μm film thickness) from J&W Scientific. Helium was used as carrier gas at a flow-rate of 0.45 mL/min. Sample injection was in the splitless mode with an injection volume of 2 μL. The GC oven temperature program was optimized: initial temperature of 70° C. was held for 2 min and then ramped at 10° C./min to 220° C. It was maintained at this temperature till the end of the run (33 min). The injection port temperature was set at 250° C. and that of the FID detector was set at 300° C. The hydrogen and air flow rates were set at 40 mL/min and 400 mL/min respectively.

Figure 2:
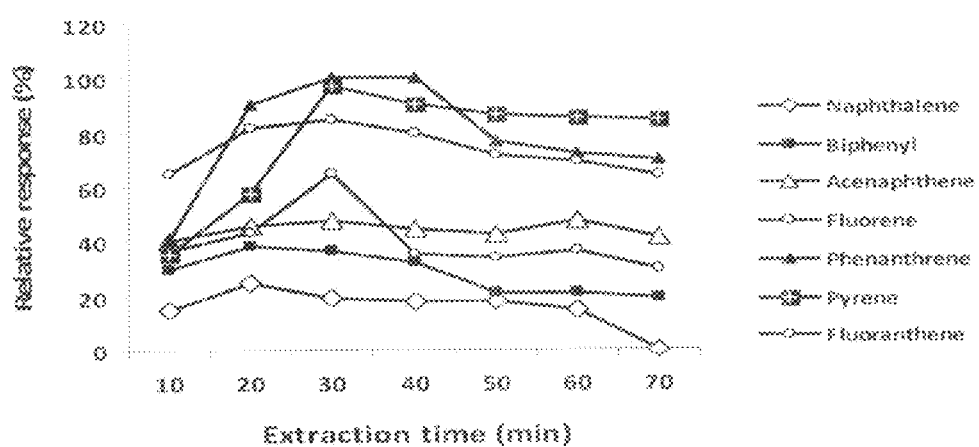
FIG. 2 is a graph illustrating the effect of extraction time on the relative response of various PAHs under specific experimental conditions.

To optimize the effect of different extraction time on the efficacy of the method, an experiment was performed by keeping all other conditions constant and varying the extraction time from 10 to 70 min. Results are given in FIG. 2 where a graph shows the effect of extraction time on the relative response of seven PAHs at experimental conditions of 5 mL sample volume (20 ng/mL), 5 min desorption in DCM (1004) and 50 mg $CaCO_3$ nanocrystals as sorbent.

30 min appeared to be the sufficient time that would allow optimal interaction between the PAHs and the nano-porous crystals. Increasing the extraction time beyond the 30 min resulted in negative to no apparent effect on most of the analytes. At longer extraction time (>30 min), heat produced by the ultrasonication would negatively affect the D-μ-SPE process. Hence 30 min was adopted during subsequent trials.

Extraction was performed in the absence of any solvent and compared to the results obtained in the presence of five different conditioning solvents. The presence of solvent has significantly enhanced the extraction procedure. Although some compounds performed relatively better in other solvents, only toluene was able to extract all seven analytes simultaneously.

Figure 3:
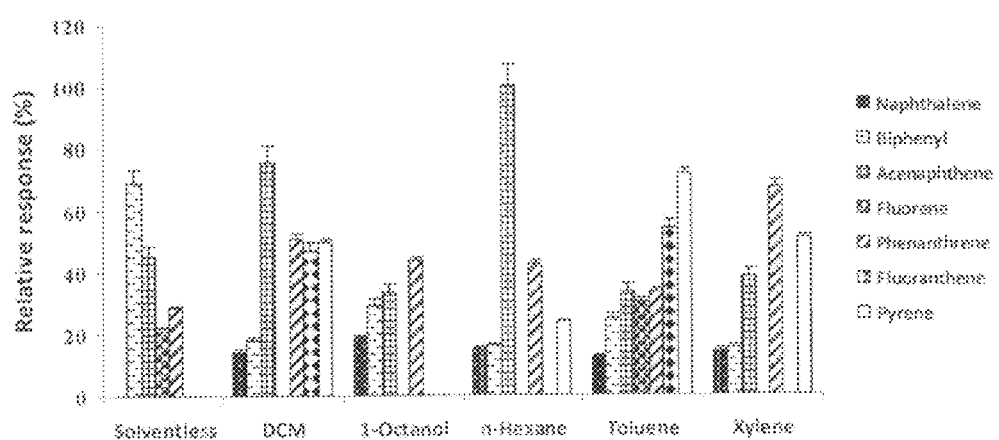
FIG. 3 is a graph illustrating the effect of various conditioning solvents on the relative response of various PAHs under specific experimental conditions.

FIG. 3 illustrates the effect of various conditioning solvents on the relative response of seven PAHs at the following experimental conditions: 5 mL sample volume (20 ng/mL), 10 min ultrasonic extraction, 5 min desorption time and 50 mg $CaCO_3$ nanocrystals as sorbent. Hydrophobic interaction (Z. C. Zeledon-Toruno et al., "Removal of PAHs from water using an immature coal (leonardite)", *Chemosphere* vol. 67, no. 3, pp. 505-512, 2007-incorporated herein by reference in its entirety) seems to govern the sorption of PAHs to the porous nanocrystals. The better performance of the extraction procedure with toluene might be due to its better facilitation of the interaction of these non-polar analytes with the hydrophobic hollow spaces within the nanocrystals. Although both xylene and toluene contain an aromatic ring, the latter solvent has lower viscosity which enabled it to have a better interaction with both the analytes and the hydrophobic pores of the sorbent. Toluene was then selected as conditioning solvent in subsequent experiments.

Various performance criteria including enhancement factor (EF) of the extraction procedure (the ratio of peak areas for extracted sample relative to un-extracted one), relative standard deviation (RSD, n=3); linearity and limit of detection (LOD) (at signal-to-noise ratio, S/N=3) were used to assess the performance of this method. Table 1 shows linearity of the detector response between the concentrations of 0.05 and 30 ng/mL, with coefficient of determination ranging from 0.9853 to 0.9953.

TABLE 1

Method parameters using D-μ-SPE and GC-FID for PAHs determination in water.

| PAHs | Slope ± SD | Intercept ± SD | $R^{2\,a}$ | $LOD^b$ (ng/mL) | $LOQ^c$ (ng/mL) | $EF^d$ | RSD (%), n = 3 |
|---|---|---|---|---|---|---|---|
| Naphthalene | 1.02 ± 0.03 | 4.79 ± 0.13 | 0.9953 | 0.022 | 0.073 | 1433 | 2.71 |
| Biphenyl | 0.46 ± 0.02 | 6.23 ± 0.31 | 0.9857 | 0.012 | 0.04 | 567 | 4.88 |
| Acenaphthene | 1.04 ± 0.10 | 11.02 ± 1.10 | 0.9853 | 0.008 | 0.027 | 968 | 9.96 |
| Fluorene | 0.95 ± 0.05 | 10.48 ± 0.62 | 0.9939 | 0.01 | 0.033 | 682 | 5.65 |
| Phenanthrene | 1.33 ± 0.14 | 6.64 ± 0.72 | 0.9939 | 0.008 | 0.027 | 839 | 11.21 |
| Fluoranthene | 0.72 ± 0.09 | 97.57 ± 10.70 | 0.9950 | 0.006 | 0.02 | 1376 | 12.5 |
| Pyrene | 0.64 ± 0.64 | 10.23 ± 1.02 | 0.9973 | 0.004 | 0.013 | 388 | 10.51 |

[a] Coefficient of determination for 0.05-30 ng/mL
[b] LOD, limit of detection at S/N = 3
[c] LOQ, limit of quantitation at S/N = 10
[d] EF, enhancement factor (ratio of peak area for extracted sample relative to un-extracted one)

The instrument responsivity was greatly enhanced by the high EF of the extraction method. In addition, the repeatability of this method is good as signified by RSD of <13%. LOD (ng/mL) values of the different analytes were obtained at S/N of 3, with pyrene having the lowest value of 0.004. The LODs are low enough for the successful determination of the PAHs in water. For quantitative determination of the analytes, the limits of quantitation (LOQ) were estimated from S/N equaled 10.

Figure 4:
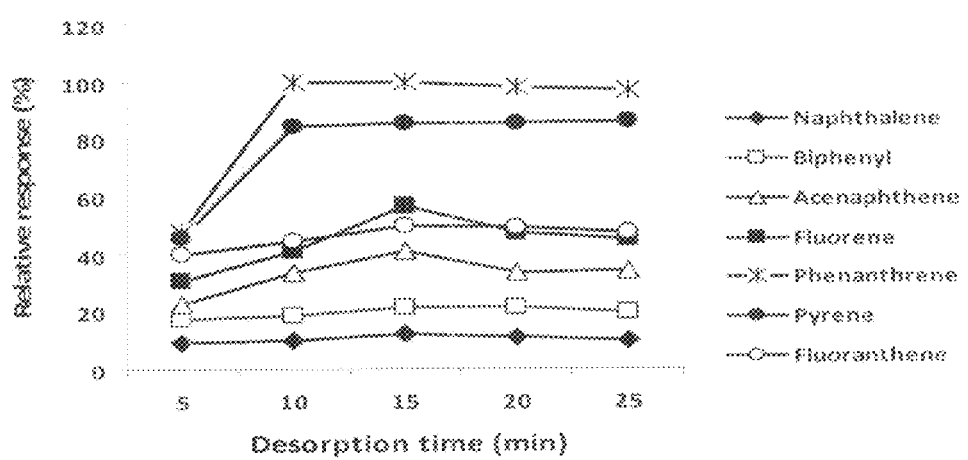
FIG. 4 is a graph illustrating the effect of desorption time on the relative response of various PAHs under specific experimental conditions.

After the extraction, desorption was performed in 100 µL of DCM at five different times: 5, 10, 15, 20 and 25 min. FIG. 4 illustrates the effect of desorption time on the relative response of seven PAHs at the following experimental conditions: 5 mL sample volume (20 ng/mL), 30 min extraction time, and 50 mg $CaCO_3$ nanocrystals as sorbent. According to FIG. 4, no significant difference in the relative responses of biphenyl and naphthalene between 5 and 25 min. However, both pyrene and phenanthrene were desorbed at the optimum time of 10 min, while 15 min was necessary for acenaphthene, fluorene and fluoranthene desorption. Consequently, 15 min was taken as desorption time in the remaining parts of this study.

Five pH values (2, 4, 7, 9 and 12) were examined in order to study their effect on the D-µ-SPE method. Results obtained show generally no significant difference in the peak areas of the analytes when the extraction procedure was performed at the acidic and basic pH values as compared to the neutral pH. This indicates the absence of significant impact of pH on the analytes which may be explained from the lack of ionizable groups on the PAHs. As a result, all subsequent trials in this study were performed at neutral pH. Nanoporous $CaCO_3$ crystals are easily soluble at very low sample pH (<2).

FIGS. 5A-5C illustrate the PAHs extraction chromatograms. FIG. 5A illustrates SPE extract of 20 ng/mL spiked ultrapure water sample. FIG. 5B illustrates 2 µg/mL standard chromatogram (without extraction). FIG. SC illustrates D-µ-SPE-GC-FID of 20 ng/mL spiked water sample. For FIGS. 5A-5C, the peak identification is the same in each graph according to the following: 1. Naphthalene, 2. Biphenyl, 3. Acenaphthene, 4. Fluorene, 5. Phenanthrene, 6. Fluoranthene, 7. Pyrene.

Characteristics of the $CaCO_3$ nanocrystal-based D-µ-SPE-GC-FID method can be seen to compare favorably with previously reported techniques in the literature as seen in Table 2 below.

Figure 5:
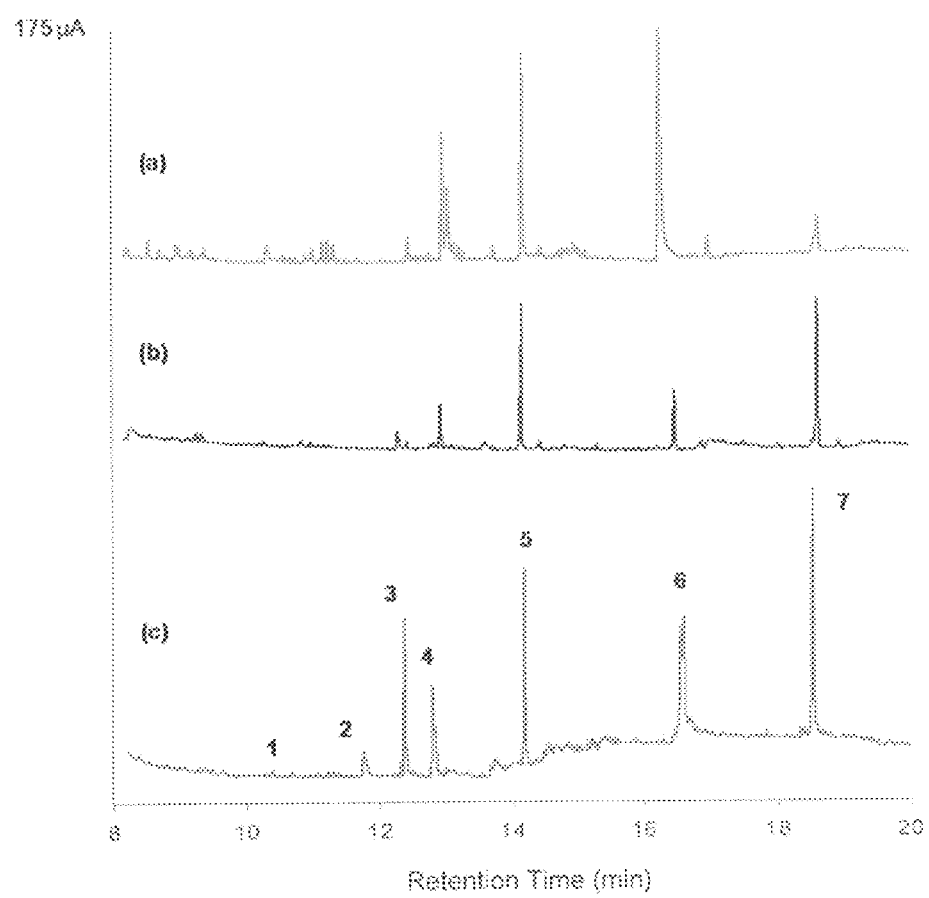
FIG. 5 is an extraction chromatogram depicting various PAH spikes under specific experimental conditions.

Extraction performance of D-µ-SPE is comparable with previously established microextraction techniques (Y-N. Hsieh, et al., "Nafion membrane-supported ionic liquid-solid phase microextraction for analyzing ultra trace PAHs in water samples" Analytica Chimica Acta, vol. 557, no. 1-2, pp. 321-328, 2006; P. Poppet al., "Application of stir bar sorptive extraction in combination with column liquid chromatography for the determination of polycyclicaromatic hydrocarbons in water samples", Analytica Chimica Acta, vol. 436, no. 1, pp. 1-9, 2001; L. Oliferova et al., "On-line solid-phase extraction and HPLC determination of polycyclic aromatic hydrocarbons in water using fluorocarbon polymer sorbents" Analytica Chimica Acta, vol. 538, no. 1-2, pp. 35-40, 2005— each incorporated herein by reference in its entirety). As shown in FIG. 5, both D-µ-SPE and SPE techniques showed comparable extractions performance. However, SPE required longer extraction time and huge amount of organic solvents. Table 3, illustrated below, shows the percentage recoveries of D-µ-SPE and SPE techniques spiked at same concentrations (5 ng/mL).

TABLE 3

Relative recoveries (% RR) of D-µ-SPE, SPE and the mean concentration of PAHs detected using D-µ-SPE of real water analysis

| PAHs | % RR of SPE 5 ng/mL spiked sample | % RR of D-µ-SPE 5 ng/mL spiked sample | Mean PAHs concentration detected from Dammam real water samples (ng/mL, n = 10) |
| --- | --- | --- | --- |
| Naphthalene | 90 ± 3 | 92 ± 3 | 1.06 ± 0.02 |
| Biphenyl | 107 ± 5 | 110 ± 4 | 0.15 ± 0.01 |
| Acenaphthene | 84 ± 8 | 85 ± 8 | 1.90 ± 0.18 |
| Fluorene | 100 ± 6 | 104 ± 5 | 0.36 ± 0.02 |
| Phenanthrene | 90 ± 10 | 92 ± 10 | 3.22 ± 0.33 |
| Fluoranthene | 86 ± 10 | 87 ± 10 | 13.43 ± 1.54 |
| Pyrene | 94 ± 10 | 96 ± 10 | 0.43 ± 0.04 |

The percentage relative recoveries (ratio of the peak area for spiked seawater sample to that of spiked ultrapure water) indicate the absence of negative matrix effect. The optimized D-µ-SPE-GC-FID method was successfully applied to the analysis of real water samples (with salinity between 38.35 and 41.45 part-per-thousand) from Dammam Port. Ten selected stations were sampled around the Dammam Port. Four stations were located inside the port operational area and two each in either side of the port. Two stations were sampled inside the shipping lane. This port is the main gateway through which cargoes from all over the world enter the

TABLE 2

$CaCO_3$ nanoporous crystal-based D-µ-SPE -GC-FID method characteristics as compared with literature

| Method | SV[a] | ET[b] | LOD (ng/L) | % RSD | RR[c] | N[d] | Ref |
| --- | --- | --- | --- | --- | --- | --- | --- |
| IL-SPME-GC-MS[e] | 10 | 40 | 4-5 | 6.1-11.4 | 80-110 | 5 | [Hsieh, 2006] |
| SBSE-LC-FLD[f] | 10 | 60 | 0.2-2 | 4.7-13.5 | 58-100 | 15 | [Popp, 2001] |
| SPE-HPLC-UV[g] | 20 | 20 | 5-40 | 1-6 | 94-106 | 5 | [Oliferova, 2005] |
| D-µ-SPE -GC-FID | 5 | 30 | 4-22 | 2.7-12.5 | 84-110 | 7 | Present |

[a]Sample volume (mL)
[b]Extraction time (min)
[c]relative recovery (%)
[d]Number of PAHs determined
[e]Nafion membrane-supported ionic liquid-solid phase microextraction (SPME) with GC-MS
[f]stir bar sorptive extraction(SBSE) and liquid chromatography (LC) with fluorescence detection
[g]Online-SPME with LC and ultraviolet detection Eastern and Central Provinces of the Kingdom. The Port is fully self-sufficient with mechanical and marine workshops, water treatment plants and about 39 berths. It is one of the busiest ports in Saudi Arabia. Around the port, artisan and small fishing boats are operated for both commercial and recreational purposes. The nearby Dammam Corniche is considered to be highly polluted with sewage discharges and other inputs from agricultural and rain waters. PAHs concentrations between 0.15±0.01 and 13.43±1.54 ng/mL were found (Table 3).

Nanoporous polymorphic crystals of $CaCO_3$ were used as sorbent and were applied in the dispersive micro-solid-phase extraction of selected PAHs as target analytes. After separation of the analytes on gas chromatography, they were successfully quantified with external calibration using flame ionization detection. Different factors controlling the extraction procedures were investigated. Results have shown that in addition to solvent type, extraction and desorption time have a significant effect on the method performance. Comparison results have shown that this method serves as a less costly and more viable alternative to other techniques that use commercial sorption materials. The method was successfully applied to the determination of PAHs in real water samples with promising results.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for dispersive micro solid phase extraction, comprising:
   ultrasonically conditioning a nanoporous vateritic calcium carbonate with a solvent to form a calcium carbonate mixture;
   mixing an aqueous solution containing one or more polycyclic aromatic hydrocarbons with the calcium carbonate mixture to adsorb said polycyclic aromatic hydrocarbons on the nanoporous vateritic calcium carbonate and to form an analysis composition;
   centrifuging the analysis composition to isolate a solid fraction and a liquid fraction of the analysis composition;
   removing water from the solid fraction derived from centrifugation; and
   adding the solvent to the centrifuged solid fraction to desorb said polycyclic aromatic hydrocarbons by ultrasonication, thereby obtaining desorbed polycyclic aromatic hydrocarbons.

2. The method of claim 1, wherein said solvent is a compound having a six-membered hydrocarbon aromatic ring optionally substituted with one or more $C_1$-$C_6$ alkyl groups.

3. The method of claim 1, wherein said solvent is toluene.

4. The method of claim 1, further comprising:
   determining the polycyclic aromatic hydrocarbon content of the aqueous solution.

5. The method of claim 1, wherein said desorbed polycyclic aromatic hydrocarbons are extracted and analyzed by a gas chromatography flame ionization detector.

* * * * *